United States Patent
Choi et al.

(10) Patent No.: US 12,134,062 B2
(45) Date of Patent: Nov. 5, 2024

(54) PORTABLE AIR PURIFIER

(71) Applicant: LG ELECTRONICS INC., Seoul (KR)

(72) Inventors: Ji Eun Choi, Seoul (KR); Hyungho Park, Seoul (KR); Seongkyeol Hong, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 476 days.

(21) Appl. No.: 17/508,169

(22) Filed: Oct. 22, 2021

(65) Prior Publication Data

US 2022/0184543 A1    Jun. 16, 2022

(30) Foreign Application Priority Data

Dec. 14, 2020 (KR) .................. 10-2020-0174528
Dec. 30, 2020 (KR) .................. 10-2020-0188335

(51) Int. Cl.
*B01D 46/84* (2022.01)
*A61L 9/20* (2006.01)
(Continued)

(52) U.S. Cl.
CPC ............ *B01D 46/84* (2022.01); *A61L 9/20* (2013.01); *B01D 46/0002* (2013.01);
(Continued)

(58) Field of Classification Search
CPC .... B01D 46/84; B01D 46/0028; B01D 46/24; B01D 46/4218; B01D 46/0049; B01D 2273/30; A61L 9/20; A61L 2209/12; A61L 2209/14; A61L 2209/15; F24F 8/108; F24F 8/22
See application file for complete search history.

(56) References Cited

U.S. PATENT DOCUMENTS

2005/0163648 A1* 7/2005 Liang .................. A61L 9/20
                                                  422/186
2008/0019861 A1  1/2008 Silderhuis
                      (Continued)

FOREIGN PATENT DOCUMENTS

CN    107101307    8/2017
CN    108367087    8/2018
                  (Continued)

OTHER PUBLICATIONS

Japanese Notice of Allowance dated Dec. 19, 2023.
(Continued)

*Primary Examiner* — Robert Clemente
(74) *Attorney, Agent, or Firm* — KED & ASSOCIATES

(57) ABSTRACT

A portable air purifier is provided that may include a housing having an inlet forming a passage through which air is suctioned into the housing, a filter disposed at an upper side of the inlet and configured to purify air suctioned in through the inlet and flowing upward, an irradiator disposed at a lower side of the filter, installed at a height at which the irradiator overlaps the inlet and configured to irradiate light for sterilization onto the filter, and a sterilizer support configured to support the irradiator and configured to be fixed to the housing and disposed around an outer perimeter of the irradiator.

21 Claims, 12 Drawing Sheets

(51) Int. Cl.
    *B01D 46/00*      (2022.01)
    *B01D 46/24*      (2006.01)
    *B01D 46/42*      (2006.01)

(52) U.S. Cl.
    CPC ......... *B01D 46/0049* (2013.01); *B01D 46/24* (2013.01); *B01D 46/4218* (2013.01); *A61L 2209/12* (2013.01); *A61L 2209/14* (2013.01); *A61L 2209/15* (2013.01); *B01D 2273/30* (2013.01)

(56) References Cited

U.S. PATENT DOCUMENTS

| | | | |
|---|---|---|---|
| 2015/0064069 A1 | 3/2015 | Yi et al. | |
| 2016/0303272 A1 | 10/2016 | Koo et al. | |
| 2019/0240371 A1* | 8/2019 | Benedek | B01D 53/8675 |

FOREIGN PATENT DOCUMENTS

| | | |
|---|---|---|
| CN | 109323342 | 2/2019 |
| CN | 111397019 | 7/2020 |
| CN | 111412416 | 7/2020 |
| JP | 2005-334162 | 12/2005 |
| JP | 2011-198473 | 10/2011 |
| JP | 2015-051268 | 3/2015 |
| JP | 2019-005094 | 1/2019 |
| JP | 2019-103963 | 6/2019 |
| JP | 2020-171739 | 10/2020 |
| KR | 10-2016-0065389 | 6/2016 |
| KR | 10-2017-0051181 | 5/2017 |
| KR | 10-2018-0079766 | 7/2018 |
| KR | 10-2019-0102538 | 9/2019 |
| KR | 10-2020-0037187 | 4/2020 |
| KR | 10-2020-0075412 | 6/2020 |
| KR | 10-2132859 | 7/2020 |

OTHER PUBLICATIONS

Japanese Office Action dated Dec. 20, 2022.
Korean Office Action dated Aug. 28, 2022 issued in Application No. 10-2020-0188335.
European Search Report dated May 9, 2022.
Taiwan Office Action dated Jul. 7, 2022.
Chinese Office Action dated Apr. 27, 2023 issued in Application No. 202110863783.6.
Chinese Office Action dated Mar. 13, 2024 issued in Application No. 202110863783.6.

* cited by examiner

PORTABLE AIR PURIFIER

CROSS-REFERENCE TO RELATED APPLICATION(S)

This application claims priority to and the benefit of Korean Patent Application No. 10-2020-0174528 filed in Korea on Dec. 14, 2020, No. 10-2020-0188335 filed in Korea on Dec. 30, 2020, the disclosures of which are incorporated herein by reference in their entirety.

BACKGROUND

1. Field

A portable air purifier, and more specifically, a portable air purifier that uses light (light rays for sterilization) to sterilize a filter are disclosed herein.

2. Background

Air purifiers are devices that are widely used in our daily lives. The devices can filter physical particles, such as dust, fine dust, and ultra fine dust, for example, chemical substances, such as odorant particles, and harmful gases, for example, and microorganisms, such as germs, and viruses, for example, to purify air.

People cannot live without air purifiers in an industrial society as more and more people are greatly affected by fine dust and suffer from allergies. Accordingly, there is a growing demand for the devices. Additionally, as living standards improve, the demand for the air purifiers grows.

Ordinarily, a large-sized air purifier is used in a house that is 100 square meters or greater. The air purifier can be provided with a filter for physical particles, such as dust, for example, a filter for chemical substances, such as gas, for example, and a filter for microorganisms, such as germs, and viruses, for example. That is, such a large-sized air purifier capable of accommodating various types of filters can be used in a large space.

However, the large-sized air purifier is rarely used in a small space, such as a studio apartment, or a space in a vehicle, for example, considering space availability, mobility, and energy efficiency. Additionally, a user who moves from place to place usually uses a small-sized air purifier. Under these circumstances, there is a growing need for a portable air purifier that is easy to carry.

The portable air purifiers need to be small and lightweight enough for users to carry, such that users may easily carry and use the portable air purifiers anywhere. That is, the portable air purifiers are useful for people who often go out and move from place to place instead of staying in one place, such as a house.

In KR Patent Publication No. 10-2020-0037187 (hereinafter, "prior art document"), which is hereby incorporated by reference, air is suctioned into a rear surface of a portable air purifier and is discharged from a front surface of the portable air purifier. The air suctioned into the rear surface of the portable air purifier may be discharged from the front surface of the portable air purifier through a filter and an air blowing fan.

A portable air purifier has a limited size such that a user carries the portable air purifier readily. Accordingly, the portable air purifier is not provided with an additional sterilizer for sterilizing the filter inside of a housing.

Further, when light is used to sterilize the filter, a portion of the light can leak out of the housing. Furthermore, when light is used to sterilize the filter, a proper incident angle and an irradiation distance of the light cannot be properly ensured due to a limited size of the housing. As a result, the filter cannot be sterilized properly.

BRIEF DESCRIPTION OF THE DRAWINGS

Embodiments will be described in detail with reference to the following drawings in which like reference numerals refer to like elements, and wherein.

DETAILED DESCRIPTION

Figure 1:
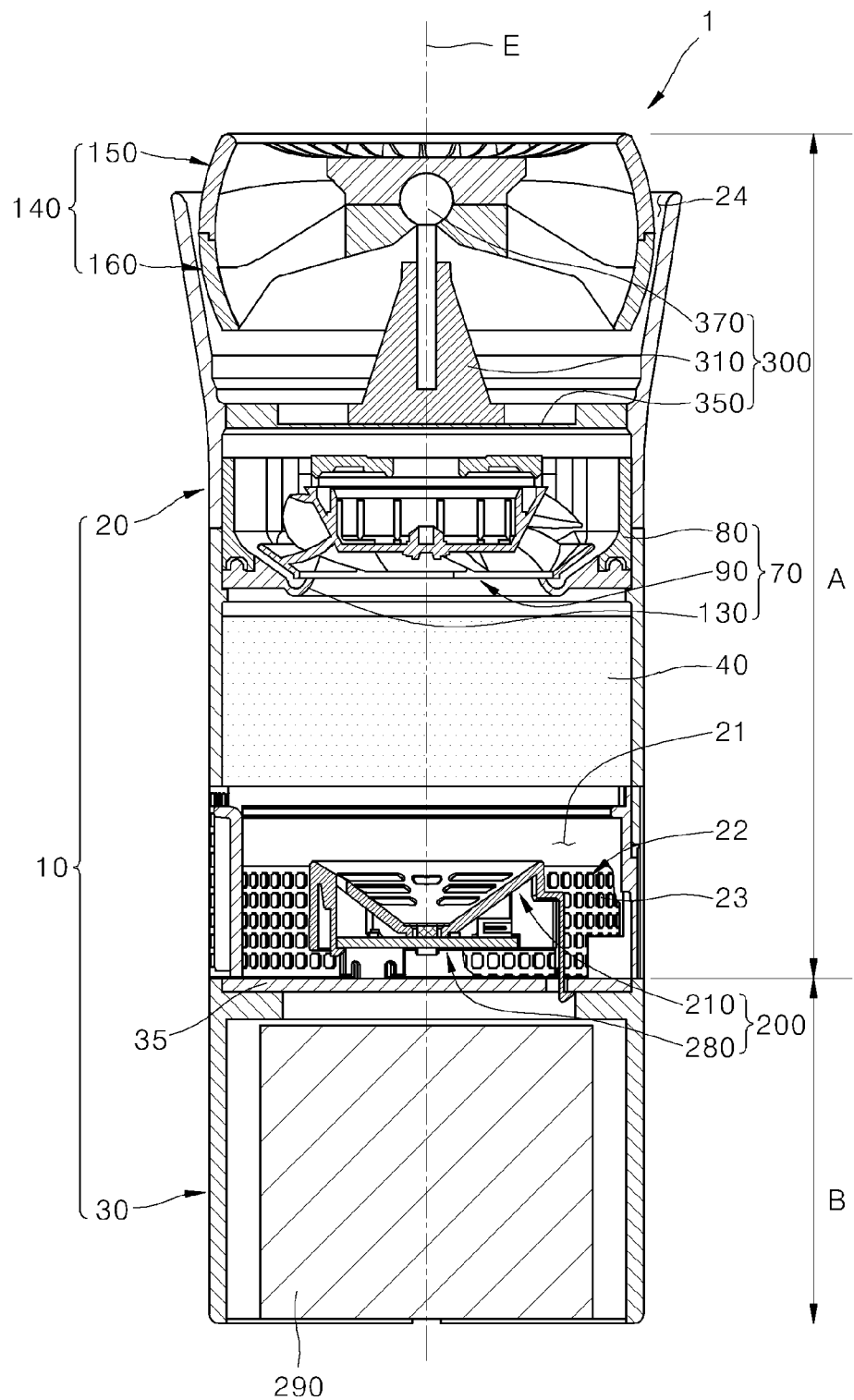
FIG. 1 is a cross-sectional view of a portable air purifier according to an embodiment.

Features and advantages are specifically described hereinafter with reference to the accompanying drawings such that one having ordinary skill in the art to which embodiments pertain may easily implement the technical spirit. Hereinafter, detailed description of known technologies in relation to the subject matter of the embodiments has been omitted if it is deemed to make the gist unnecessarily vague. Below, embodiments are specifically described with reference to the accompanying drawings. In the drawings, identical reference numerals can denote identical or similar components.

The terms "first", "second" and the like are used herein only to distinguish one component from another component. Thus, the components should not be limited by the terms. Certainly, a first component can be a second component unless stated to the contrary.

When one component is described as being "in an upper portion (or a lower portion)" of another component, or "on (or under)" another component, one component can be disposed on the upper surface (or under the lower surface) of another component, and an additional component can be interposed between another component and one component on (or under) another component.

When one component is described as being "connected", "coupled", or "connected" to another component, one component can be directly connected, coupled or connected to another component. However, it is also to be understood that an additional component can be "interposed" between the two components, or the two components can be "connected", "coupled", or "connected" through an additional component.

Hereinafter, each component can be provided as a single one or a plurality of ones, unless explicitly stated to the contrary.

The singular forms "a", "an" and "the" are intended to include the plural forms as well, unless explicitly indicated otherwise. It should be further understood that the terms "comprise" or "include" and the like, set forth herein, are not interpreted as necessarily including all the stated components or steps but can be interpreted as excluding some of the stated components or steps or can be interpreted as including additional components or steps.

Hereinafter, the terms "A and/or B" as used herein can denote A, B or A and B, and the terms "C to D" can denote C or greater and D or less, unless stated to the contrary.

Figure 2:
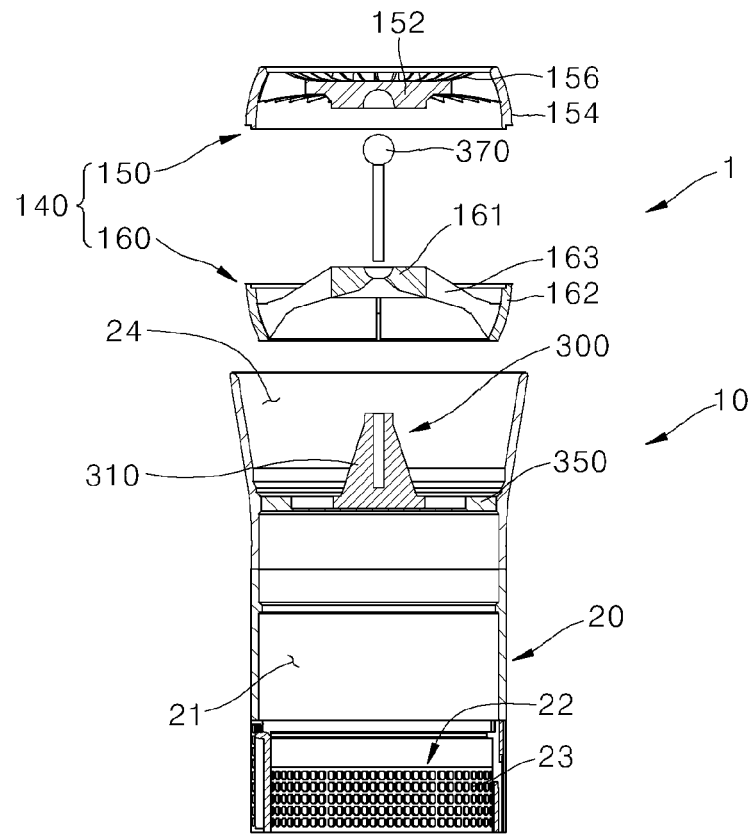
FIG. 2 is an exploded, cross-sectional view of the portable air purifier of FIG. 1.
Figure 2:
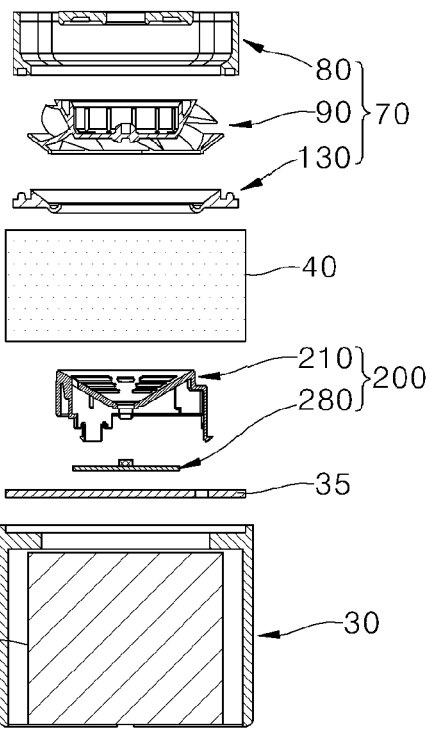
Figure 3:
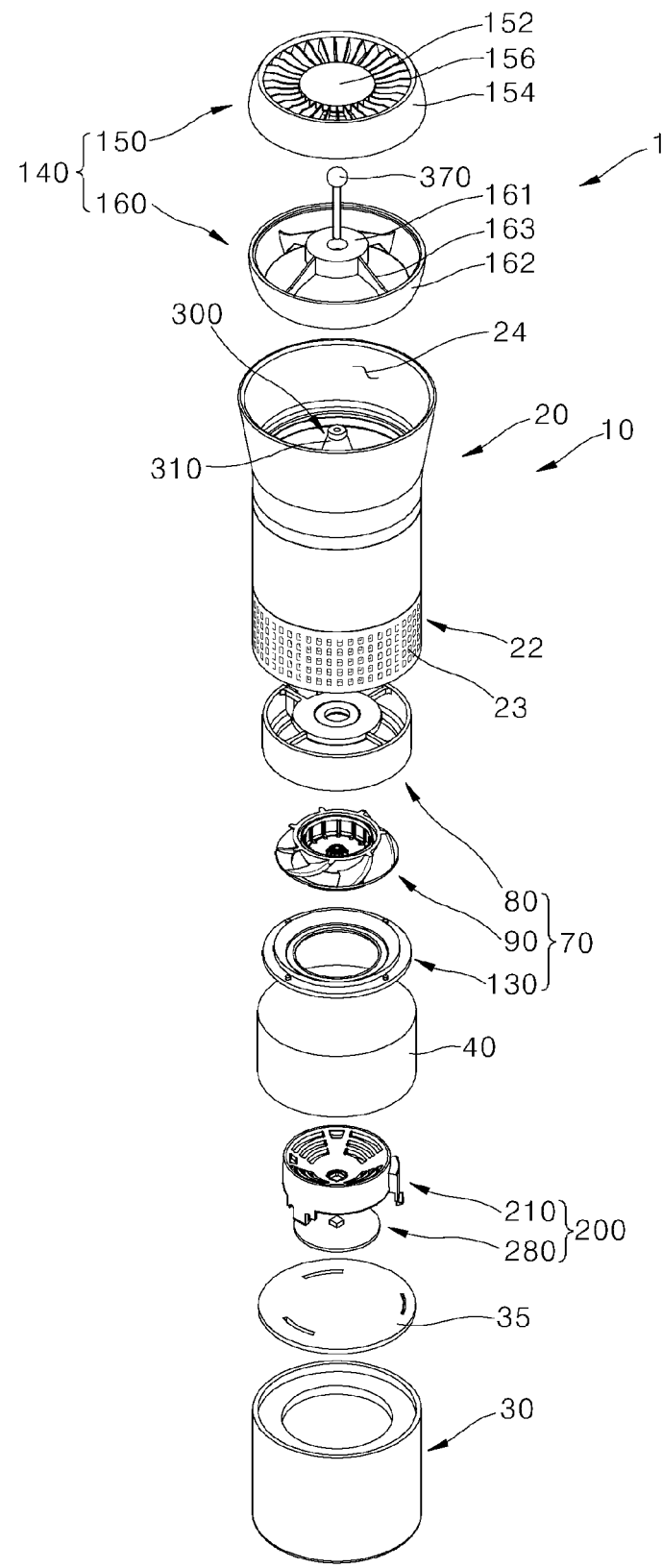
FIG. 3 is an exploded, perspective view of the portable air purifier of FIG. 1.
Figure 4:
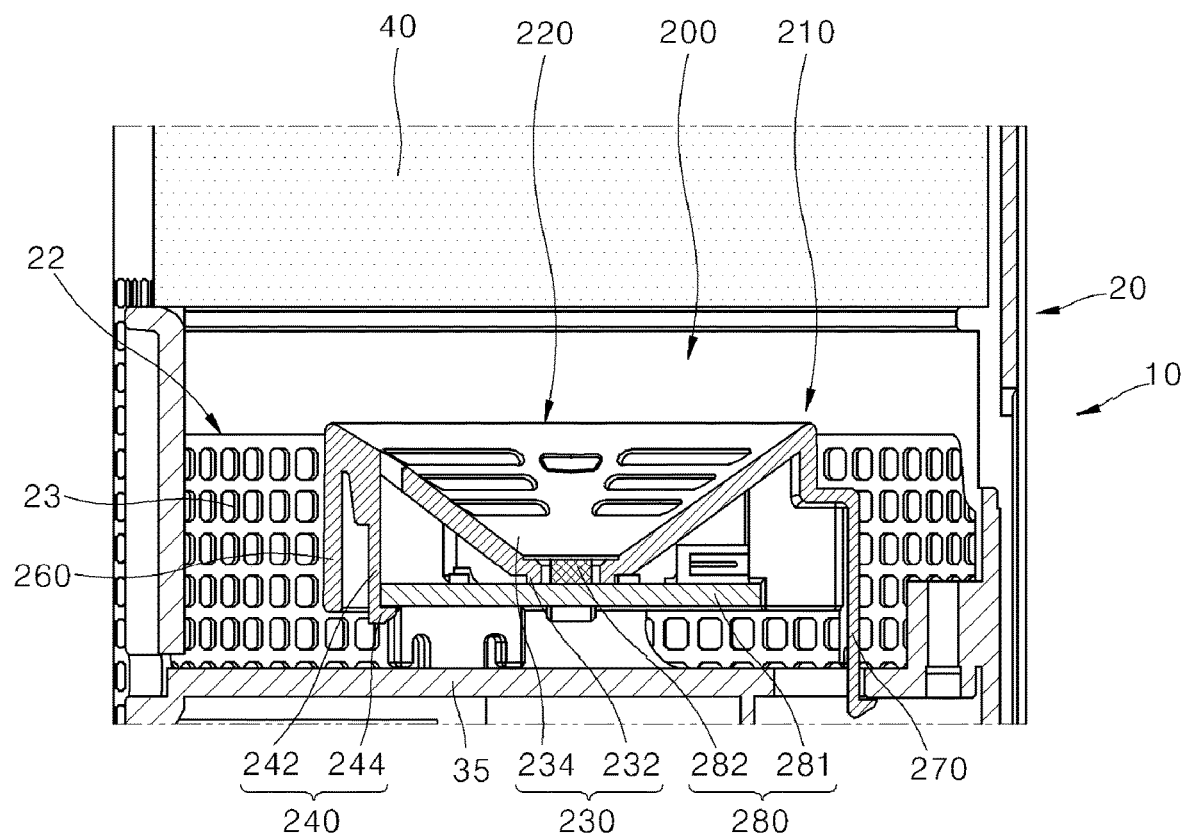
FIG. 4 is a cross-sectional view of a sterilizer of the portable air purifier of FIG. 1 installed on an inner side of a housing, facing an inlet.
Figure 5:
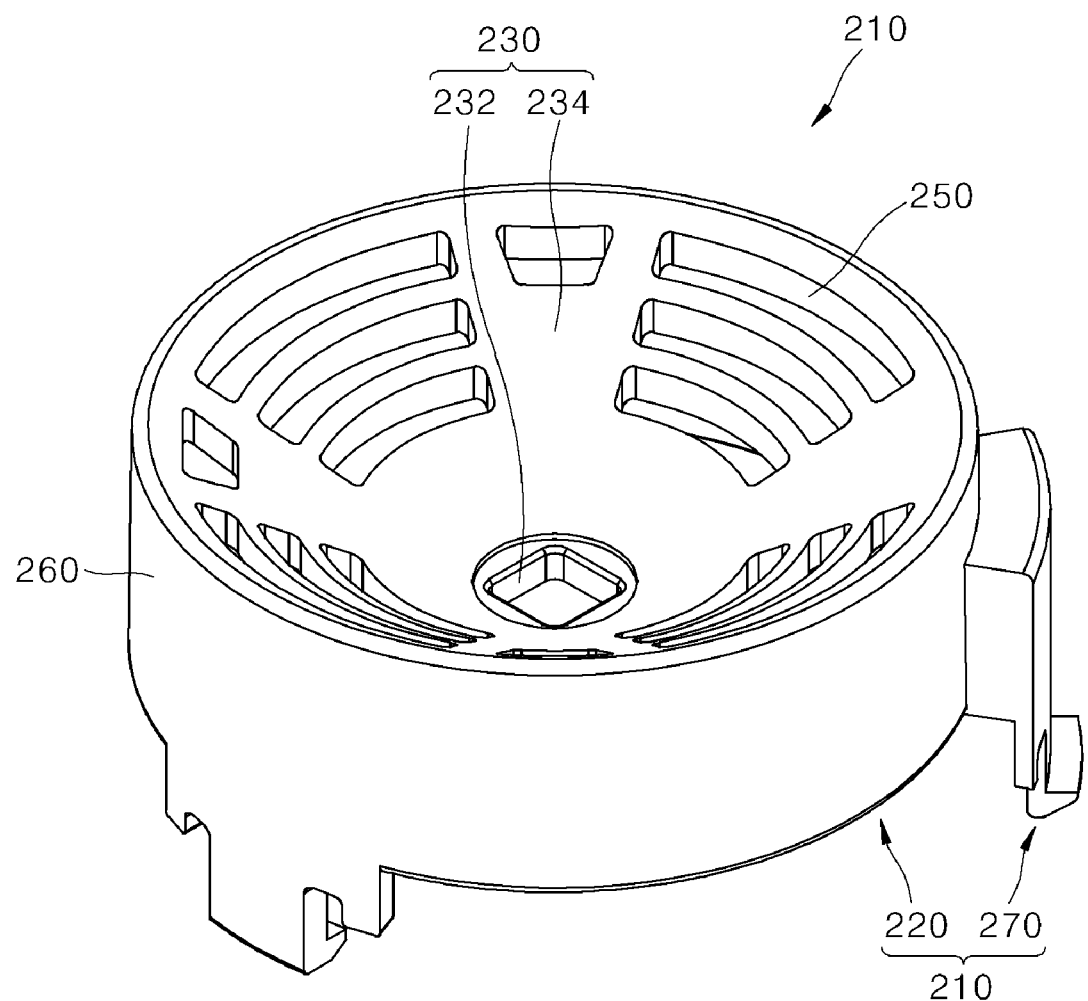
FIG. 5 is a perspective view of an upper portion of a sterilizer support of the portable air purifier of FIG. 1.
Figure 6:
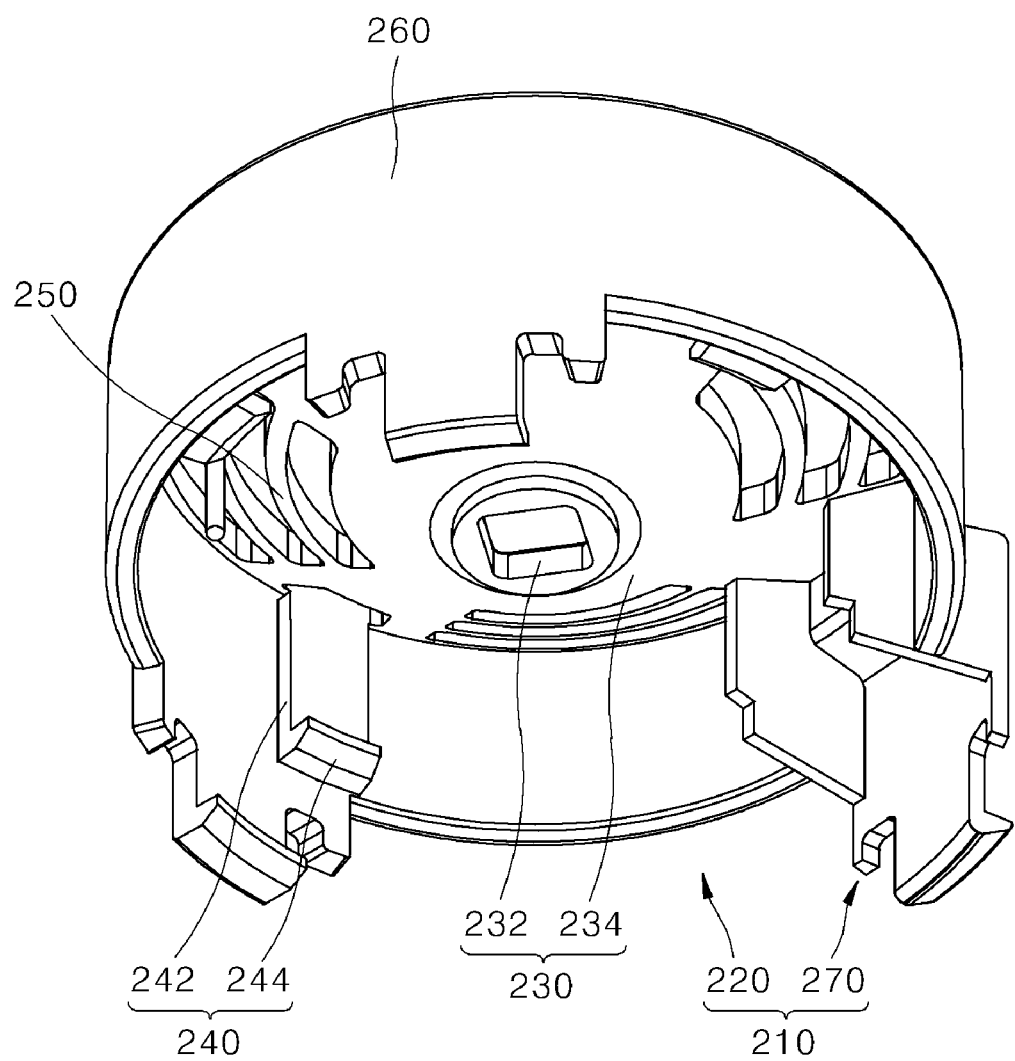
FIG. 6 is a perspective view showing a lower portion of the sterilizer support of the portable air purifier of FIG. 1.

FIG. 1 is a cross-sectional view of a portable air purifier according to an embodiment. FIG. 2 is a cross-sectional view of the portable air purifier of FIG. 1. FIG. 3 is a exploded perspective view of the portable air purifier of FIG. 1.

As illustrated in FIGS. 1 to 3, the portable air purifier 1 of embodiment may have an approximately cylindrical shape. The portable air purifier 1 may include at least one of a housing 10, a filter 40, a fan module 70, a discharge 140, a sterilizer 200, and a rotation supporter 300.

The housing 10 may be provided with an inlet 22, and provided therein with the filter 40, the sterilizer 200, and the fan module 70. The housing 10 may form an air flow path in an upward-downward direction. As the air flow path having a cylindrical shape is formed inside of the housing 10, frictional resistance of air moving in the upward-downward direction may decrease.

Additionally, centers of the inlet 22, the filter 40, the sterilizer 200, the fan module 70, the rotation supporter 300, and an outlet 24 may be aligned in the upward-downward direction along a rotational axis extending line E that passes through the center of the housing 10 in the upward-downward direction. Accordingly, air moving along the housing 10 from a lower side to an upper side may flow linearly in a perpendicular direction, resulting in a decrease in the length of the flow path of the air, and flow resistance of the air may decrease, thereby improving air purification efficiency.

The rotational axis extending line E may be the same as a rotational center of a fan included in the fan module 70, and may be aligned with a perpendicular reference line that passes through the center of the hosing 10 and extends in the upward-downward direction. When the portable air purifier 1 is placed on a horizontal surface, the perpendicular reference line may be aligned with a perpendicular line or the rotational axis extending line E. The housing 10 may include a single member, or a plurality of members, for example.

The portable air purifier 1 may be entirely formed into a cylinder that is elongated in the upward-downward direction and stands upright. Accordingly, a user may use the portable air purifier 1 in a state in which the portable air purifier 1 lies or stands. Further, the portable air purifier 1 may be used in a state in which the portable air purifier 1 is installed in a groove, such as a cup holder which is concave downward, in a location, such as a rocking vehicle. Thus, the portable air purifier 1 may be reliably disposed in its place.

Directions are defined as follows. Under the assumption that a portion in a direction in which the discharge 140 is disposed with respect to first case 20 is defined as an upper portion, and a portion in a direction in which second case 30 is disposed with respect to the first case 20 is defined as a lower portion, a "first direction" denotes the upward-downward direction or an axial direction. The first direction may be referred to as a perpendicular direction. Additionally, a "second direction" denotes a direction perpendicular to the first direction, that is, a left-right direction, a horizontal direction, or a radial direction.

The portable air purifier 1 in this embodiment may include housing 10, filter 40, fan module 70, and sterilizer 200. The portable air purifier 1 may further include discharge 140, and a battery 290.

The housing 10 may include first case 20 and second case 30. The first case 20 and the second case 30 may form a skeleton of an exterior of the portable air purifier 1. Exteriors of lateral and bottom surfaces of the portable air purifier 1 may be formed by the first case 20 and the second case 30. The first case 20 and the second case 30 may be provided therein with an accommodation space 21. The accommodation space 21 may accommodate the filter 40, the fan module 70, the sterilizer 200, the rotation supporter 300, and electronic components including the battery 290, for example. The first case 20 and the second case 30 may have enough strength to protect the accommodated components from an external impact, for example.

The filter 40 may be installed in the accommodation space 21 of the first case 20 and disposed between the fan module 70 and the inlet 22. That is, the filter 40 may be disposed under/below the fan module 70 and may purify air suctioned through the inlet 22 of the portable air purifier 1. The air, which is purified while passing through the filter 40, may pass through the fan module 70 and the discharge 140 and may be discharged from an upper portion of the portable air purifier 1.

The filter 40, disposed on or at an upper side of the inlet 22 and configured to purify air suctioned into the inlet 22 and moving upward, may be installed inside of the first case 20 to face the inlet 22. The filter 40 may be formed into a cylinder that is elongated in the upward-downward direction.

As the filter 40 is disposed on the upper side of the inlet 22, the filter 40 may not be seen from the inlet 40. Additionally, a predetermined distance may be set between an upper end of the inlet 22 and a lower end of the filter 40. The distance may be determined considering an incident angle and an irradiation distance of light (light rays for sterilization) irradiated from an irradiator 280. Additionally, the distance may also be determined considering reflectivity and performance of a reflector 230.

The filter 40 may include a single filter, or when necessary, may include of a plurality of filters in a state of being stacked. The filter 40 may be further provided with a filter case (not illustrated). The filter case may be fixed to an inside of the first case 20 and may be provided therein with an insertion space for accommodating a filter.

The fan module 70 may be accommodated in the accommodation space 21 of the first case 20 and disposed between the discharge 140 and the filter 40. More specifically, the fan module 70 may be disposed between the outlet 24 and the filter 40. That is, the fan module 70 may be disposed on/over the filter 40, and the outlet 24, the rotation supporter 300, the discharge 140 and a rotation guide 400 may be disposed on/over the fan module 70. The fan module 70 may suction air introduced into a lower portion of the filter 40 through the inlet 22 and discharge the air from the upper portion of the first case 20.

A rotational center of the discharge 140 may be aligned with a center of the fan module 70 in the upward-downward direction. The air suctioned through the inlet 22 may pass through the filter 40, the fan module 70, a guide vane 356, and the discharge 140 consecutively while moving upward, and may be discharged from an upper side of the portable air purifier 1.

In this embodiment, the fan module 70 includes a mixed flow fan, for example. The fan module 70 may suction the air having passed through the filter 40 in an axial direction and discharge the air in a direction between the axial direction and a radial direction.

The discharge 140 may be rotatably disposed on or at an upper side of the first case 20 and may guide a discharge direction of air moved upward through the outlet 24. The rotation supporter 300 may be disposed on/over the first case 20, and the discharge 140 may be rotatably disposed at/mounted onto the rotation supporter 300. The discharge 140 may have upper and lower sides which are both open, and air moved to a lower portion of the discharge 140 through the rotation supporter may be discharged out of the portable air purifier 1 through an upper portion of the discharge 140.

The sterilizer 200 may be disposed under/below the filter 40 and fixed to at least one of the first case 20 or the second case 30. The sterilizer 200 may be spaced a predetermined distance apart from the filter 40, and irradiate light (light rays for sterilization) toward the filter 40. The light irradiated by the sterilizer 200 is harmful to the human body. Accordingly, a position of the sterilizer 200 may be determined such that the light does not leak out of the portable air purifier 1 through the inlet 22. As the sterilizer 200 may be disposed on an inner side of the housing 10, facing the inlet 22, an exterior of the housing 10 need not be scaled up despite installation of the sterilizer 200, thereby making it possible to provide a compact-sized portable air purifier 1 and sterilize the filter 40.

The battery 290 may be installed in the accommodation space 21 provided inside of the second case 30 and disposed under/below the sterilizer 200. The battery 290 may supply power for driving the portable air purifier 1.

The accommodation space 21 provided in the portable air purifier 1 may be divided into a first area A and a second area B. When the accommodation space 21 is divided in the upward-downward direction, an upper area may be the first area A, and a lower area may be the second area B. The first area A and the second area B may be conceptually divided areas rather than physically divided areas.

In one embodiment, the accommodation space 21 in the first case 20 and the accommodation space 21 in the second case 30, which form the skeleton of the portable air purifier 1, may be the first area A and the second area B, respectively. Components in relation to the suction, purification, discharge, and sterilization of air may be disposed in the first area A. That is, the inlet 22, the filter 40, the fan module 70, the rotation supporter 300, the discharge 140, and the sterilizer 200 for sterilizing the filter 40 may be disposed in the first area A. Accordingly, in the first area A, air may flow from the lower side to the upper side, and a discharge direction of air may be adjusted through the discharge 140 that is rotatably installed.

The inlet 22 may be installed in the first case 20, and the inlet 22 may be provided with a plurality of inlet holes 23 as a passage for suctioning air. The outlet 24 as a passage for discharging air purified in the first area A, and the discharge 140 rotatably disposed at/mounted onto the rotation supporter 300 may be disposed on/over the first case 20. Accordingly, the first case 20 may be provided therein with an air flow path that connects the filter 40, the fan module 70, and the discharge 140.

Additionally, the sterilizer 200 may be disposed in an inner space of the housing 10, facing the inlet 22. Accordingly, the housing 10 need not be scaled up to install the sterilizer 200, and space availability may be improved.

That is, the inlet 22, the filter 40, the fan module 70, the discharge 140, the sterilizer 200, and the outlet 24 may be installed in the first area A. A passage for allowing air, suctioned into the portable air purifier 1, to pass through the air purifier may be formed in the first area A.

Components that do not directly relate to a flow of air for air purification may be disposed in the second area B. That is, a controller including a printed circuit board (PCB), and the battery 290, for example, may be installed in the second area B.

In this embodiment, the housing 10 may be formed into a cylinder having a vertical length greater than a lateral width. The first area A in the upper portion may have a vertical length greater than a vertical length of the second area B in the lower portion. That is, in the portable air purifier 1 that stands vertically, the first area A in the upper portion may be greater than the second area B in the lower portion.

The discharge 140 may be rotatably disposed at/mounted onto the rotation supporter 300. Accordingly, a discharge direction of air purified in the upper portion of the portable air purifier 1 may be readily adjusted, and air purified in the portable air purifier 1 may reach the face of the user more readily.

When the portable air purifier 1 is placed and used on a surface lower than a face of a user, the portable air purifier 1 may stand vertically rather than lie transversely to allow more air, purified in the portable air purifier 1, to reach the face of the user. When air is discharged from the upper portion of the portable air purifier 1 through the discharge 140 rotated in a predetermined direction in a state in which the portable air purifier 1 stands vertically, more air purified in the portable air purifier 1 may reach the face of the user.

As the sterilizer support 210 is arranged along a perimeter of the irradiator 280, light for sterilization aimed at the filter 40 may be blocked from being irradiated out of the housing 10 through the inlet 22. The irradiator 280 may be provided with reflector 230 around an outer perimeter thereof, and light irradiated from the irradiator 280 to the filter 40 may be prevented from being irradiated out of the inlet 22 and may be guided and irradiated to a lower side of the filter 40 by the reflector 230.

The portable air purifier 1 according to this embodiment may include at least one of housing 10, filter 40, fan module 70, discharge 140, and sterilizer 200. The portable air purifier 1 according to this embodiment may further include rotation supporter 300 and battery 290.

The housing 10 may include first case 20 and second case 30. The first case 20 may be provided with accommodation space 21 therein and inlet 22 through which air is suctioned on a lateral surface of a lower portion thereof. The first case 20 may be formed into a cylinder and have upper and lower sides that are open. The first case 20 may include a single component or member, or when necessary, a plurality of components or members. Each component or member may be fitted-coupled, coupled using an adhesive, or welded, for example, and may be coupled in various ways, such as a connection using fastening member or fastener 195 including a bolt, for example.

Air may be suctioned through the lateral surface of the lower portion of the first case 20 and discharged through an upper side of the first case 20. The inlet 22 provided with inlet holes 23 may be disposed along a perimeter of a lower portion of the first case 20. The first case 20 may be provided with outlet 24 for discharging air, on the upper side thereof.

In a state in which the inlet 22 for suctioning air is disposed around an outer perimeter of the first case 20, filter 40 may be disposed on an upper side such that the filter 40 is spaced from the inlet 22. Accordingly, air may move uniformly across an entire surface of the filter 40.

The inlet 22 may be provided with a plurality of inlet holes 23. The inlet hole 23 may be disposed at a slant in an oblique line shape, and when necessary, formed into an inequality sign. The inlet hole 23 may be modified in various ways. For example, to increase a flow rate of air flowing into the filter 40, the inlet hole 23 may be additionally formed on a lateral surface of the housing 10, on which the filter 40 is disposed. The housing 10 may be modified in various ways. For example, the housing 10 may include three or more members.

The second case 30 may connect to the lower portion of the first case 20, and may be modified in various ways within the technical scope in which the second case is provided therein with a space in which electronic components including battery 290 may be installed.

At least one of the first case 20 or the second case 30 may be formed into a cylindrical case. The first case 20 and the second case 30 may both be formed into a cylinder or the second case 30 only may be formed into a cylinder. When necessary, the first case 20 only may be formed into a cylinder.

In the case of second case 30 having a cylindrical shape and extending in the upward-downward direction, the user may readily hold an outer perimeter of the second case 30 in hand, and the second case 30 may be easily held in a vehicle cup holder provided with a groove having a circular cross section. In the case of first case 20 having a cylindrical shape, friction, caused as a result of contact between air, which moves upward while passing through the first case 20, and an inside of the first case 20 having a curved shape, may be reduced, thereby enabling the air to flow more smoothly.

Additionally, an air flow path may be formed inside of the first case 20, and no air flow path may be formed inside of the second case 30. Accordingly, air may be smoothly suctioned and discharged through the first case 20 even when the second case 30 is held in the cup holder or the user's hand, thereby ensuring improvement in usability and convenience.

An inner housing 35 that supports sterilizer 200 may be disposed on the second case 30. The inner housing 35 may be a plate and may support a lower portion of the sterilizer 200. The inner housing 35 according to this embodiment may be a circular plate, and may shield an upper side of the second case 30.

The inner housing 35 may be fixed to at least one of the first case 20 or the second case 30 and provided with a hole to fix a support bracket 270 of the sterilizer 200.

The inner housing 35 may be disposed between the first case 20 and the second case 30 and may shield the lower portion of the first case 20. Additionally, the inner housing 35 may be disposed on a lower side of the sterilizer 200, and may be modified in various ways within the technical scope in which the inner housing 35 connects to the housing 10 and movement of the inner housing is restricted. Air suctioned into the first case 20 through the inlet 22 may be blocked from moving to the second case 30 by the inner housing 35 such that a flow rate of air moving to the fan module 70 increases, thereby ensuring improvement in air purification performance of the portable air purifier 1.

The filter 40 may be disposed inside of the first case 20 and may be modified in various ways within the technical scope in which the filter purifies air suctioned into the inlet 22. The filter 40 according to this embodiment may be formed into a cylinder.

The first case 20 may be a circular pipe, and the filter 40 installed in the first case 20 may be a cylinder in contact with the inside of the first case 20. Accordingly, impurities in air passing through the first case 20 may be removed effectively.

A transverse cross section of the filter 40 may have a circular shape, and the filter 40 may have a largest area in the first case 20. Additionally, the filter 40 may be a cylinder, and when upper and lower ends of cloth of the filter 40 are cut, pressure loss may be minimized, and performance of the filter 40 may be maximized.

An outer diameter of the filter 40 may be greater than a diameter of an entrance through which air is suctioned into the fan module 70. Accordingly, a volume of the filter 40 may be maximized.

In this embodiment, the filter 40, the fan module 70, the sterilizer 200, and the discharge 140 may be disposed along the housing 10 in the upward-downward direction, and air may also flow in the upward-downward direction. That is, air may flow linearly in a direction the same as the direction in which the filter 40, the fan module 70, and the discharge 140 are disposed, as a result of operation of the fan module 70.

When air flows linearly, resistance against an air flow may decrease, and air may flow more smoothly. Thus, a sufficient amount of air may be suctioned and discharged by the fan module 70, and air purification performance of the portable air purifier 1 may improve.

An antimicrobial HEPA filter may be used as the filter 40 according to this embodiment. When power is not properly supplied to the sterilizer 200, irradiator 280 may not operate, and the filter 40 may not be sterilized correctly. To solve this problem, a HEPA filter to which an antimicrobial agent is applied may be used as the filter 40.

The fan module 70 may be disposed between the filter 40 and the outlet 24, and may be modified in various ways within the technical scope in which the fan module rotates a fan to blow air toward the outlet 24. When a circular mixed flow fan module is employed as the fan module 70, the first case 20 need not be scaled-up despite fixation or a coupling of the fan module 70 as the shape of the fan module 70 matches or corresponds to the cylindrical shape of the inside of the first case 20, thereby making a product smaller. Additionally, when the portable air purifier 1 according to this embodiment is applied to a vehicle, the portable air purifier 1 may be small enough to fit into a cup holder.

As the circular mixed flow fan module is employed as the fan module 70, a small-sized upward discharge-type air purifier, which ensures maximized hydrodynamic performance, may be provided. A fan of the fan module 70 may include a mixed flow fan, and an inner structure of the fan module 70 may change to mount the mixed flow fan.

Fan 90 according to this embodiment may rotate as a result of operation of a motor. A rotational shaft of the motor configured to rotate the fan 90 may only connect to the fan 90. A rotor may be installed in the fan 90, and a stator may be installed in fan housing 80, rotation of which is restricted. As a magnetic field of the stator changes, the shaft connected to the fan 90 may rotate along with the rotor such that the rotor and the fan 90 rotate around the stator. The configuration of the motor for rotating the fan 90 is well known. Thus, detailed description thereof has been omitted.

The fan module 70 according to this embodiment may include fan housing 80, fan 90, and fan base 130. The fan housing 80 may be fixed to the inside of the first case 20, and may be modified in various ways within the technical scope in which the fan housing is provided therein with a space for rotating the fan 90. The fan 90 may be rotatably installed in the fan housing 80, and may be modified in various ways within the technical scope in which the fan moves air toward the discharge 140.

In one embodiment, a mixed flow fan is employed as the fan 90; however, embodiments are not limited thereto. Another type of fan may also be used as the fan 90 according to embodiments.

The fan base 130 may be coupled to a lower side of the fan housing 80, and may be modified in various ways within the technical scope in which the fan base guides air having passed through the filter 40 into the fan 90. The fan base 130 may be disposed between the filter 40 and the fan 90. An edge of the fan base 130 may have a shape corresponding to a shape of an edge of the filter 40. For example, when the filter 40 has a cylindrical shape and the edge of the filter 40 has a circular shape, the fan base 130 may be formed into a ring provided with a hollow hole/may be installed in a ring shape provided with a hollow hole.

As illustrated in FIGS. 1 to 3, the discharge 140 may be rotatably disposed at/mounted onto rotation supporter 300, and may be modified in various ways within the technical scope in which the discharge 140 adjusts a discharge direction of air having passed through the fan module 70. The discharge 140 according to this embodiment may be rotatably disposed at/mounted onto a sphere-shaped ball joint 370 installed in the rotation supporter 300 and may rotate smoothly.

The discharge 140 may be open in the upward-downward direction and may rotatably connect to the rotation supporter 300. Accordingly, the discharge 140 may adjust a discharge direction of air having passed through the fan module 70. The discharge 140 according to this embodiment may include a first discharge 150 and a second discharge 160.

The first discharge 150 may be disposed on one side of the ball joint 370 (an upper side in FIG. 2), and may be modified in various ways within the technical scope in which the first discharge 150 is provided with a plurality of vanes 156 configured to guide discharge of air. The first discharge 150 according to this embodiment may include a first discharge core 152, a first discharge body 154, and the vane 156.

The first discharge core 152 may surround an upper side of the sphere shape of the ball joint 370 and may be disposed on an upper side of a core 310. Additionally, the first discharge body 154 may surround an outside of the first discharge core 152 in a ring shape, and an outside of the first discharge body 154 may be formed into a curved surface. As the first discharge core 152 and the first discharge body 154 may be connected by a plurality of vanes 156, the first discharge core 152, the first discharge body 154, and the vanes 156 may rotate together.

The second discharge 160 may be disposed on the other side of the ball joint 370 (a lower side in FIG. 2) and connected to the first discharge 150, and may be modified in various ways within the technical scope in which the second discharge 160 rotates around the ball joint 370 together with the first discharge 150. The second discharge 160 according to this embodiment may include a second discharge core 161, a second discharge body 162, and a discharge support 163.

The second discharge core 161 may surround a lower side of the sphere shape of the ball joint 370 and may be disposed on or at a lower side of the first discharge core 152. Additionally, the second discharge body 162 may surround an outside of the second discharge core 161 in a ring shape, and an outside of the second discharge body 162 may be formed into a curved surface.

As the second discharge core 161 and the second discharge body 162 may be connected by a plurality of discharge supports 163, the second discharge core 161, the second discharge body 162, and the discharge supports 163 may rotate together.

The rotation supporter 300 may be modified in various ways within the technical scope in which the rotation supporter 300 rotatably supports the discharge 140 disposed in the outlet 24 of the housing 10. The rotation supporter 300 according to this embodiment may include core 310, a core supporter 350, and ball joint 370.

The core member 310 may be disposed on or at a lower side of the discharge 140 and extend toward the discharge 140. The core 310 may be disposed on the lower side of the discharge 140 and be configured to adjust a discharge direction of air and extend from a center of the outlet 24 toward the discharge 140.

An outside of the core 310 may be formed into a curved surface, and a transverse cross section of the core 310 may gradually narrow from a lower side of the core 310, connected to the core supporter 350, toward the ball joint 370. Accordingly, resistance of air moving from the lower side to the upper side thereof may be minimized. Alternatively, the outside of the core member 310 may be formed into a curved surface, and may be modified in various ways. For example, a transverse cross section of the core may remain constant or change from the lower side of the core member, connected to the core supporter 350, toward the ball joint 370.

The core 310 may have a circular cone shape. The transverse cross section of the core 310 may gradually decrease toward the upper side of the core 310.

The core supporter 350 may be modified in various ways within the technical scope in which the core supporter 350 supports a lower portion of the core 310 and is fixed to the housing 10. A vane disposed at/installed in the core supporter 350 may be modified in various ways. For example, the vane may extend radially or be installed in a spiral shape with respect to the core 310.

The ball joint 370 may be modified in various ways within the technical scope in which a lower side of the ball joint 370 is coupled to the core 310 such that movement of the ball joint 370 is restricted, and an upper side of the ball joint 370 is inserted into the discharge 140 and rotatably supports the discharge 140. The ball joint 370 may have a sphere-shaped end, may be disposed inside of the discharge 140, and may rotatably support the discharge 140.

Figure 7:
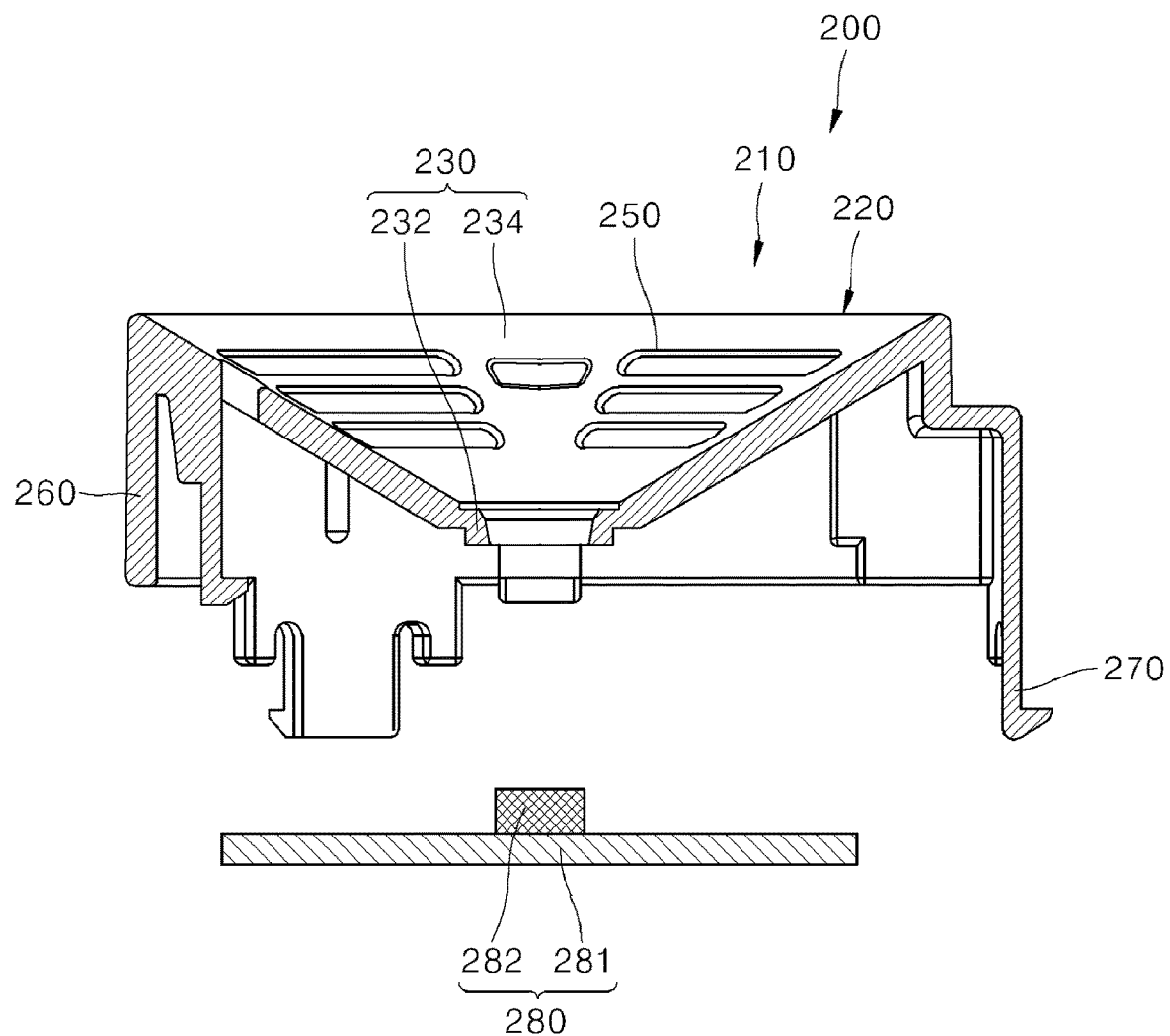
FIG. 7 is a cut-away perspective view of the sterilizer support of the portable air purifier of FIG. 1.
Figure 8:
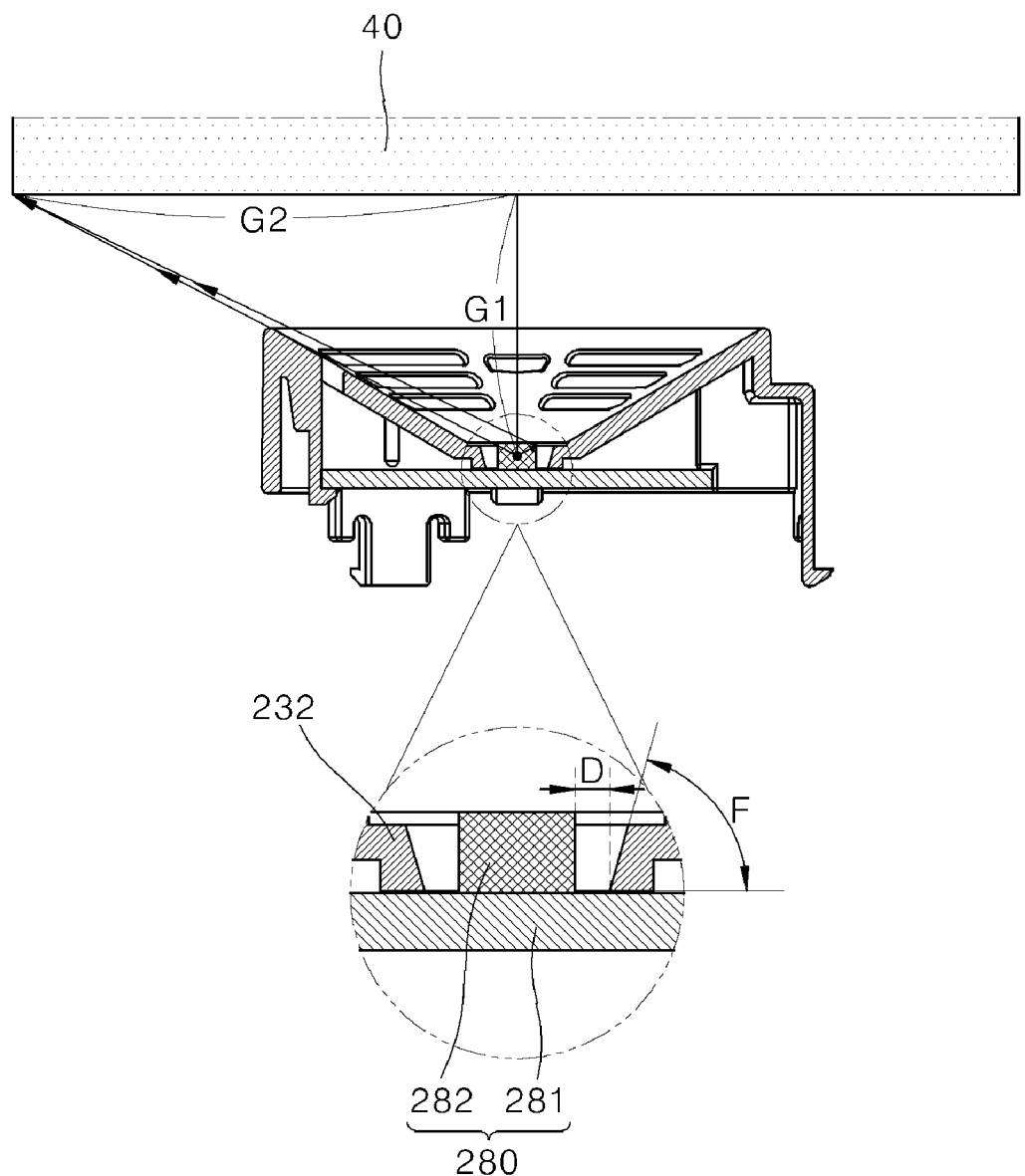
FIG. 8 is a view of the sterilizer of the portable air purifier of FIG. 1 disposed on a lower side of a filter.

FIG. 7 is a cut-away perspective view of the sterilizer support of the portable air purifier of FIG. 1. FIG. 8 is a view of the sterilizer of the portable air purifier of FIG. 1 disposed on a lower side of a filter.

As illustrated in FIGS. 1, 7 and 8, the sterilizer 200 may be disposed on or at the lower side of the filter 40 and disposed at a same height as that of the inlet 22. As the sterilizer 200 and the inlet 22 are disposed at the same height, the air purifier according to this embodiment may ensure improvement in space availability unlike an air purifier in which a sterilizer is disposed on an upper side of an inlet, and the housing 10 according to this embodiment may be disposed at a low position unlike a housing of an air purifier in which the sterilizer is disposed on the upper side of the inlet. The sterilizer 200 may be modified in various ways within the technical scope in which the sterilizer irradiates light to sterilize the filter 40. The sterilizer 200 according to this embodiment may include sterilizer support 210 and irradiator 280.

The sterilizer support 210 may be fixed to the housing 10 while supporting the irradiator 280. The sterilizer support 210 may be modified in various ways within the technical scope in which the sterilizer support is disposed around an outer perimeter of the irradiator 280. The sterilizer support 210 according to this embodiment may be fixed to at least one of the first case 20 or the second case 30. The sterilizer support 210 may include support body 220 and support bracket 270.

The support body 220 may be disposed around the outer perimeter of the irradiator 280, and may be modified in various ways within the technical scope in which the support body 220 reflects light for sterilization irradiated from a sterilizing light source 282 to the filter 40. The support body 220 according to this embodiment may include at least one of reflector 230, an inner supporter 240, a heat dissipating hole 250 and a blocking body 260.

The reflector 230 may be concave toward the filter 40 and provided with the sterilizing light source 282 of the irradiator 280 at a center thereof. The reflector 230 may reflect light irradiated from the sterilizing light source 282 of the irradiator 280 toward the filter 40.

The reflector 230 may be disposed on an inner side of the housing 10, facing the inlet 22. As ultraviolet rays used as the sterilizing light source 282 are harmful to the human body, the support body 220 including the reflector 230 may be installed to prevent light for sterilization from being irradiator out of the housing 10. The reflector 230 may be installed to block light for sterilization from being irradiated to the housing 10, which may be injection molded, except for the filter 40, or from leaking out of the housing 10 through the inlet 22. The reflector 230 may be designed considering an incident angle of light for sterilization and a surface area of the filter 40.

The reflector 230 may be a funnel, an upper side of which is open, and an upper end of the reflector 230 may be disposed on a same line as an upper end of the inlet 22 or disposed higher than the upper end of the inlet 22. Accordingly, light for sterilization irradiated from the sterilizing light source 282 may be prevented from being irradiated out of the inlet 22.

Additionally, an angle of the reflector 230 may be designed not to limit light for sterilization toward an edge of the filter 40. The reflector 230 according to this embodiment may include a first reflecting body 232 and a second reflecting body 234.

The first reflecting body 232 may be disposed along a perimeter of the sterilizing light source 282 and be spaced a predetermined distance D apart from the sterilizing light source 282. The second reflecting body 234 may extend upward from the first reflecting body 232 at a slant. The second reflecting body 234 according to this embodiment may be a funnel an upper side of which is open, and an inner diameter of the second reflecting body 234 may gradually increase from the first reflecting body 232 toward the filter 40.

A reflecting and coating layer may be formed on a surface of the reflector 230. The surface of the reflector 230, which may be injection molded may be coated with a material, such as aluminum, or chrome, for example, having high reflectivity, such that the reflector 230 serves as a reflecting plate.

The first reflecting body 232 facing the sterilizing light source 282 may only be provided with a coating layer. When necessary, the second reflecting body 234 may also be provided with a coating layer. When the reflector 230 is coated with aluminum, reflectivity may be 90%.

The reflecting surface of the first reflecting body 232, facing the sterilizing light source 282, may be installed while forming a predetermined angle F with a horizontal line. A predetermined angle F of a reflecting surface according to this embodiment may be a slant angle of 805 degrees. Accordingly, light for sterilization irradiated from the sterilizing light source 282 may be directly irradiated to the edge of the filter 40, or may reflect off the first reflecting body 232 and then be irradiated to the edge of the filter 40, thereby minimizing loss of the light for sterilization. As the reflector 230 is installed as describe above, an average illumination may improve to 6%, and a minimum illumination may improve to 26% with respect to UVC-LED 10 mW.

A predetermined distance D between sterilizing light source 282 and first reflecting body 232 according to this embodiment may be 1.4 mm 5 mm. If a distance between the sterilizing light source 282 and the filter 40 is referred to as a "first length G1" and a radius of a lower surface of the filter 40 is referred to as a "second length G2", in this case, the second length G2 according to this embodiment may be 1.8 to 2.2 times greater than the first length G1.

The inner supporter 240 may be modified in various ways within the technical scope in which the inner supporter 240 extends to a lower side of the reflector 230 and supports printed circuit board 281 of the irradiator 280. The inner supporter 240 according to this embodiment may include an inner bracket 242 extended to the lower side of the reflector 230, and a hook 244 bent inward from a lower side of the inner bracket 242 to the irradiator 282 and held at an edge of the irradiator 280.

A plurality of inner supporters 240 may be provided and extend to the lower side of the reflector 230. The inner supporter 240 may operate like a hook, and may be held at an outer edge of the printed circuit board 281. Accordingly, the printed circuit board 281 may be fixed to an inside of the support body 220.

The heat dissipating hole 250 may include a plurality of holes at the reflector 230. As air moves through the heat dissipating hole 250, the heat dissipating hole 250 may air-cool the irradiator 280. The heat dissipating hole 250 may include a plurality of long holes having a circular arc shape around the sterilizing light source 282. In the heat dissipating hole 250, a slit hole that extends in a circular arc form may be disposed around the sterilizing light source 282. As a result of the installation of the heat dissipating hole 250, the printed circuit board 281 of the irradiator 280 disposed on a lower side of the irradiator 280 may be air-cooled, thereby improving heat dissipation performance of the sterilizing light source 282 using a UVC LED.

The blocking body 260 may extend from an outer edge of the reflector 230 to the lower side thereof. The blocking body 260 may a cylinder a lower side of which is open, and centers of the blocking body 260 and the inlet 22 may be aligned with each other. As the blocking body 260 is provided, the blocking body 260 may block movement of the sterilizing light source 282 although the sterilizing light source 282 is irradiated from the irradiator 280 to the lower side of the reflector 230. Accordingly, when light for sterilization is about to be irradiated out of the housing 10 through the inlet 22, the reflector 230 may block the light primarily, and the blocking body 260 may block the light secondarily.

The support bracket 270 may be modified in various ways within the technical scope in which the support bracket 270 extends to a lower side of the support body 220 and is fixed to the housing 10. The support bracket 270 may extend to the lower side of the support body 220 and may be fixed to at least one of the first case 20 or the second case 30 or may be fixed to the inner housing 35 shielding the upper side of the second case 30.

The support bracket 270 according to this embodiment may be coupled to the inner housing 35 having a plate shape in a hook form. Accordingly, the sterilizer 200 may be installed and disassembled easily, and time and cost spent for maintenance and repair of the sterilizer 200 may decrease.

The irradiator 280 may be disposed on the lower side of the filter 40 and disposed at a height at which the irradiator 280 overlaps the inlet 22, and may irradiate light for sterilization to the filter 40. Additionally, movement of the irradiator 280 may be restricted by the sterilizer support 210 and may be on a perpendicular reference line that passes through a radius-wise center of the inlet 22 in the upward-downward direction. The perpendicular reference line and the rotational axis extending line may form the same straight line. Further, the centers of the first case 20, the filter 40, the fan module 70, and the irradiator 280 may be aligned in the upward-downward direction.

When the filter 40 is disposed on an upper side of the irradiator 280, sterilizing light source 282 that supplies a relatively small amount of light may sterilize an entire surface area of the lower end of the filter 40, thereby reducing costs incurred for manufacturing, maintenance, and repairs.

The irradiator 280 may be modified in various ways within the technical scope in which the irradiator 280 is disposed at a position higher than or the same as that of the upper end of the inlet 22. The irradiator 280 according to this embodiment may include printed circuit board 281 and sterilizing light source 282. The printed circuit board 281 may be fixed to an inside of the sterilizer support 210, and the sterilizing light source 282 configured to irradiate light for sterilization may be disposed on an upper side of the printed circuit board 281 or inside the printed circuit board 281.

The printed circuit board 281 may be held by the inner supporter 240 included in the support body 220 such that movement of the printed circuit board 281 is restricted. The sterilizing light source 282 disposed on the printed circuit board 281 may be disposed on the lower side of the filter 40 and may irradiate light for sterilization at an incident angle set to face an upper side on which the filter 40 is disposed. As radius-wise centers of the sterilizing light source 282 and the filter 40 are aligned in the upward-downward direction, light for sterilization may be uniformly irradiated to a lower portion of the filter 40. The sterilizing light source 282 may be a UVC LED, and a variety of sterilizing devices may be used within the technical scope in which the sterilizing light source sterilizes germs in the filter 40.

As the reflector 230 is disposed along the perimeter of the sterilizing light source 282 although the sterilizing light source 282 of the sterilizer 200 and the inlet 22 are disposed at the same height, light may be prevented from being irradiated out of the first case 20 through the inlet 22.

In the related art, an incident angle of the UVC LED configured to irradiate light for sterilization is limited. Accordingly, when a proper distance between the filter 40 and the UVC LED is not ensured, the edge of the filter 40 may not be sterilized by the UVC LED.

According to embodiments disclosed herein, due to the reflector 230 and the reflective coating of the reflector 230, light for sterilization may be uniformly irradiated to the lower portion of the filter 40, thereby ensuring improvement in sterilization performance. As the reflector 230 may be disposed around the outer perimeter of the irradiator 280 and in the shape of a funnel, the reflector 230 may reflect light for sterilization to the filter 40. Additionally, as reflectivity increases due to the reflective coating of the reflector 230, an incident angle and irradiation distance of light for sterilization may be ensured even in a limited space.

The inlet 22 for suctioning external air may be disposed around the outer perimeter of the first case 20. Accordingly, air outside of the first case 20 may move into the first case 20 through the inlet 22 such that a flow rate of suctioned air increases.

As a result of operation of the fan module 70, air outside of the portable air purifier 1 may flow into the portable air purifier 1. In this case, the air outside of the portable air purifier 1 may form a spiral-shaped air flow rotating around an outer perimeter of the inner supporter 240 while passing through the inlet holes 23.

The air, which flows into the first case 20 and moves upward while rotating in a spiral shape, may move up toward the filter 40, rotating around a perimeter of the sterilizer 200. Additionally, the air having passed through the filter 40 may move to an upper side of the housing 10 through the fan module 70.

While the air passes through the filter 40, physical particles, such as dust, fine dust, and ultra fine dust, for example, chemical substances, such as odorant particles, and harmful gases, for example, microorganisms, such as germs, and viruses, for example in the air may be filtered. As the filter 40, the fan module 70 and the rotation supporter 300 are disposed on one straight line in the upward-downward direction, flow loss may be minimized and air may be effectively suctioned and filtered.

Air suctioned into the fan module 70 may be discharged from an upper side of the fan module 70 and may move into the discharge 140. As the discharge 140 rotates within predetermined angles, a direction of discharged air may be adjusted depending on an angle at which the discharge 140 is installed.

Additionally, an inside of the discharge 140 may form a concave groove. Accordingly, discharge resistance of air, the direction of which is changed through the discharge 140, may decrease. Further, as the filter 40, the fan module 70, and the discharge 140 are disposed on one straight line in the upward-downward direction, flow loss of air may be minimized, air may be effectively suctioned and filtered, and purified air may be effectively discharged.

Germs in the air may be collected in the filter 40, and light for sterilization irradiated from the sterilizing light source 282 may be irradiated to the lower portion of the filter 40, light for sterilization may be directly irradiated to the filter 40, or may reflect off the reflector 230 and then be irradiated to the lower portion of the filter 40 to sterilize the filter 40.

The sterilizing light source 282 may use light having a wavelength of 275 nm that shows high sterilization efficiency as light for sterilization, and considering a UV radiation range on the surface of the filter 40 using a HEPA filter and reliability of a filter, the first length G1 as an irradiation distance may be set to 17.7 mm or so. As the filter 40 and the sterilizing light source 282 become closer, sterilization performance may improve, but after the filter 40 is used for a long time, degradation of the filter 40 may cause damage to an exterior of the filter 40 or particle removal performance of the filter 40 may deteriorate. Additionally, when an optimal distance between the filter 40 and the sterilizing light source 282 is not maintained, an amount of light reaching the edge of the filter 40 may decrease, and sterilization performance may deteriorate. With the sterilizer 200 according to embodiments disclosed herein, surface illumination may be ensured even for the edge of the filter 40, and reliability of the filter 40 may be ensured.

When the portable air purifier 1 provided with the sterilizer 200 is installed in a vehicle, germs and viruses in the vehicle may be attached to the filter 40 and then light for sterilization may be irradiated to eliminate the germs attached to the filter 40. Bacteria and viruses in polluted air suctioned in through an inlet of a vehicle may be collected using an electrostatic force of the filter 40 using a HEPA filter. Then light for sterilization may be irradiated to eliminate the bacteria and viruses collected in the filter 40.

Figure 9:
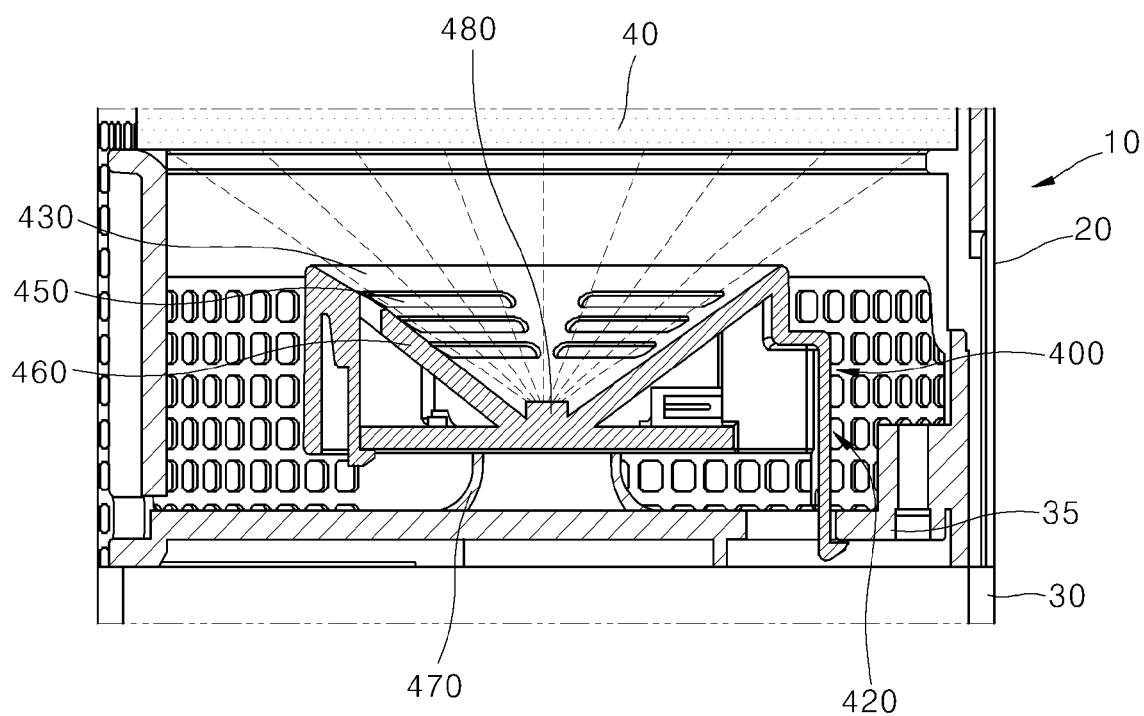
FIG. 9 is a cross-sectional view of a sterilizer according to another embodiment.
Figure 10:
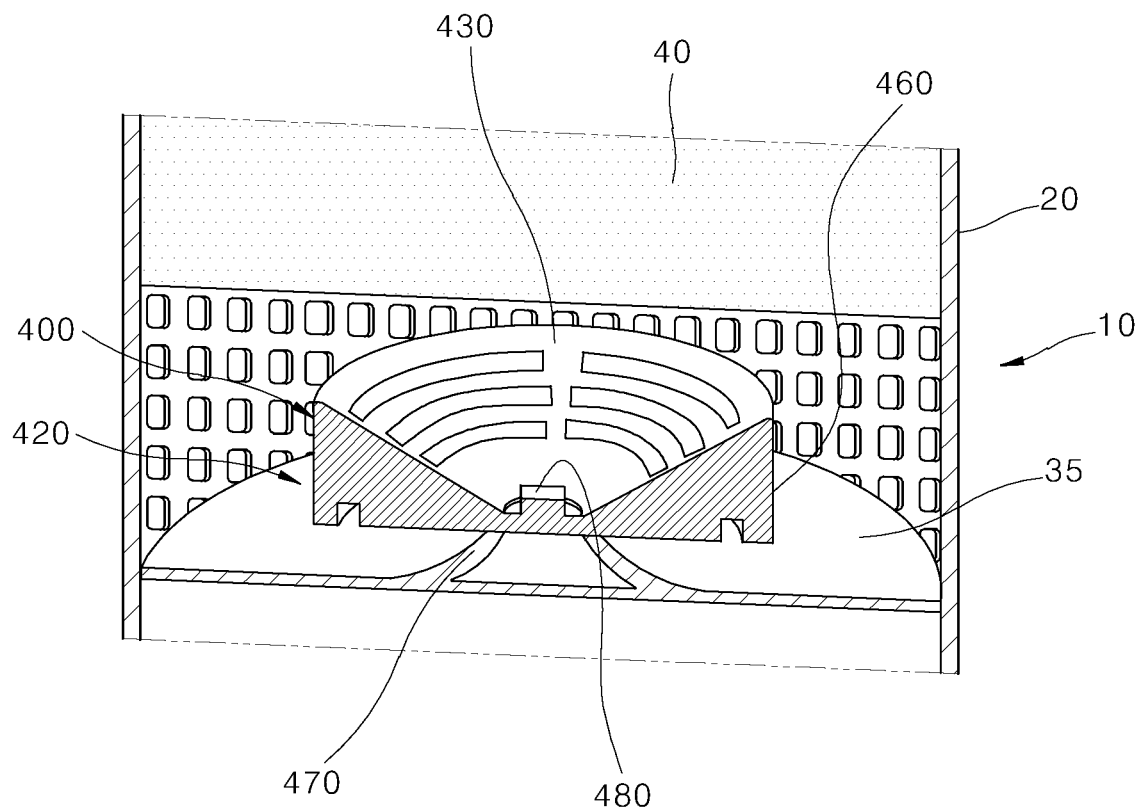
FIG. 10 is a perspective view of the sterilizer of FIG. 9.
Figure 11:
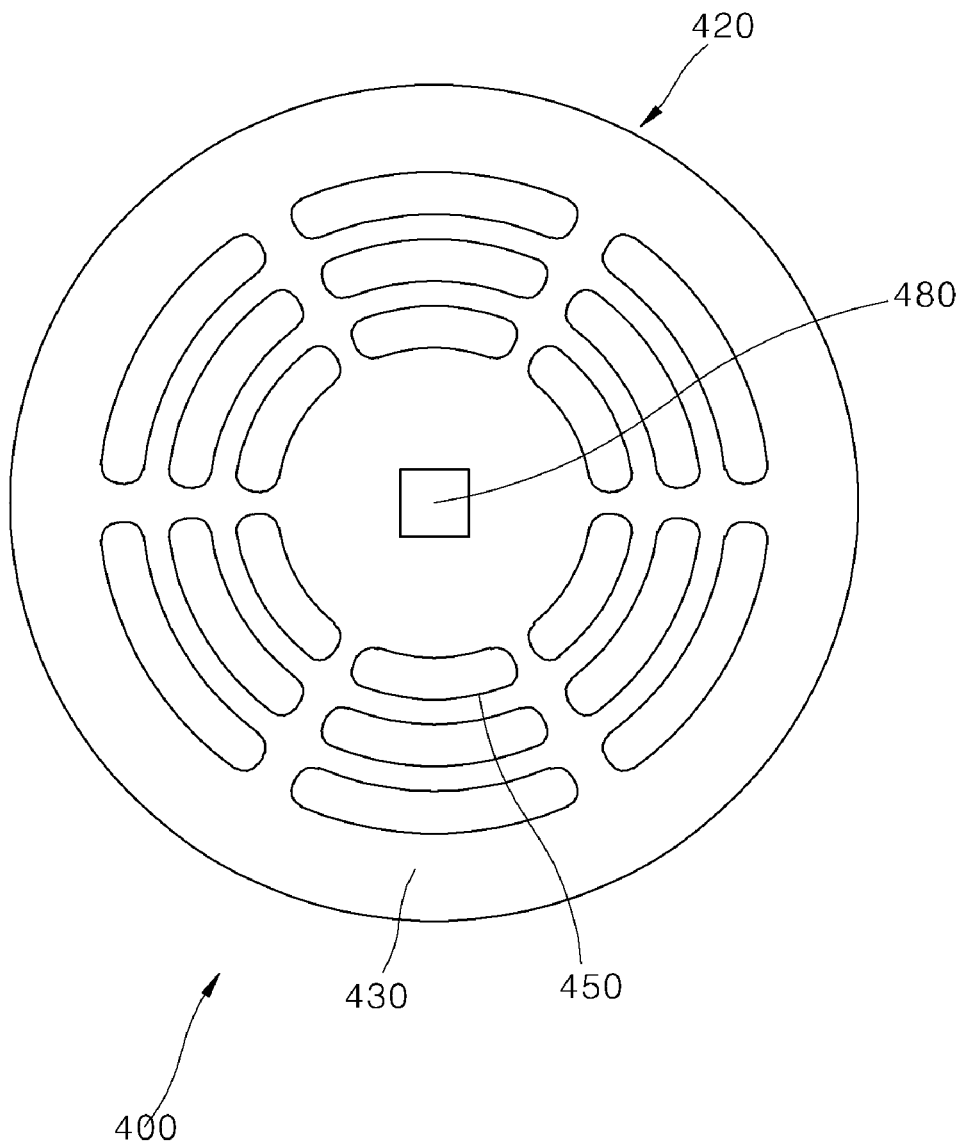
FIG. 11 is a plan view of the sterilizer of FIG. 9.

FIG. 9 is a cross-sectional view of a sterilizer according to another embodiment. FIG. 10 is a perspective view of the sterilizer of FIG. 9. FIG. 11 is a plan view of the sterilizer of FIG. 9.

As illustrated in FIGS. 9 to 11, sterilizer 400 according to this embodiment may include sterilizer support 410 and irradiator 480. The sterilizer support 410 may support a lower portion of the irradiator 480, may be disposed on an inner side of housing 10, facing inlet 22, and may include support body 420 and support 470.

The support body 420 according to this embodiment may include reflector 230, heat dissipating hole 450, and blocking body 460. The reflector 430 may be a funnel an upper side of which is open, and may be provided with the radiator 480 configured to irradiate light for sterilization at a concave center thereof.

As a plurality of heat dissipating holes 450, forming a slit hole circumferentially, is disposed at the reflector 430, the heat dissipating holes 450 may air-cool the irradiator 480 fixed to the support body 420. The reflector 430 may be provided with the blocking body 460 having a pipe shape around an outer perimeter thereof.

The support body 420 may be supported by the support 470. The support 470 may be modified in various ways within the technical scope in which the support 470 protrudes upward from a center of inner housing 35 and supports a lower portion of the support body 420. The support 470 may be disposed at a center of the inlet 22 in a radial direction thereof, and a transverse cross section of the support 470 may have a circular shape to reduce friction between the support 470 and air.

The support 470 may be formed into a pillar that protrudes upward from the center of the inner housing 35. The support 470 may be formed into a cylinder or a circular cone. The support 470 according to this embodiment may have a transverse cross section that gradually becomes narrow from a lower side to an upper side, and as the support 470 is disposed at a center of first case 20, where the inlet 22 is formed, friction between the support 470 and air may be minimized.

The transverse cross section of the support 470 may have a circular shape, and air suctioned through the inlet 22 may move to an upper side on which filter 40 is disposed while rotating along an outside of the support 470. That is, the sterilizer 400 may be disposed in a central portion of the first case 20, and air suctioned through the inlet 22 may move up while rotating around an outer perimeter of the sterilizer 400. Accordingly, flow resistance of the sterilizer 400 may decrease.

A radius-wise center of the support 470, a rotational center of fan 90 and a radius-wise center of the filter 40 may be on one straight line in the perpendicular direction. In this case, resistance against a flow of air moving from the lower side to the upper side may decrease, and air may flow more smoothly. Thus, the portable air purifier 1 may ensure improvement in air purification performance.

Figure 12:
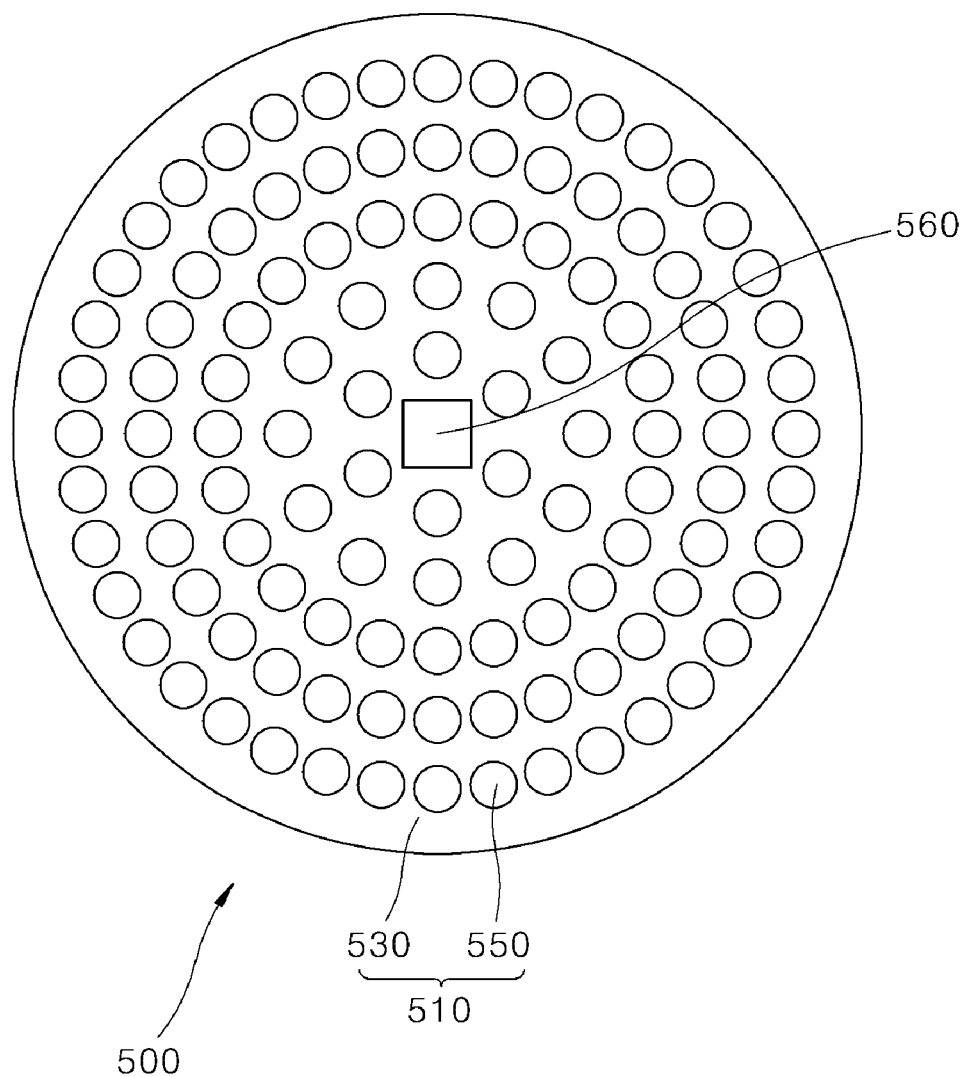
FIG. 12 is a plan view of a sterilizer according to still another embodiment.

FIG. 12 is a plan view of a sterilizer according to still another embodiment. As illustrated in FIG. 12, sterilizer 500 according to this embodiment may include sterilizer support 510 and irradiator 560. The sterilizer support 510 may include reflector 530 and heat dissipating hole 550, and the irradiator 560 configured to irradiate light for sterilization may be disposed at a concave center of the reflector 530.

The reflector 530 may be provided with a plurality of heat dissipating holes 550 forming a circular hole. Accordingly, the heat dissipating holes 550 may air-cool the irradiator 560 fixed to the sterilizer support 510. The heat dissipating holes 550 may be formed into various shapes including a triangle, and a polygon, for example, and may be modified in various ways within the technical scope in which the heat dissipating holes 550 air-cools the irradiator 560.

Embodiments disclosed herein are directed to a portable air purifier in which a sterilizer for sterilizing a filter may be installed in a housing. Embodiments disclosed herein are further directed to a portable air purifier that may block light for sterilization aimed at a filter from being irradiated out of a housing. Embodiments disclosed herein are also directed to a portable air purifier in which an incident angle and an irradiation distance of light for sterilization aimed at a filter may be ensured despite a limited size of a housing.

Advantages according to embodiments disclosed herein are not limited to the above ones, and other aspects and advantages that are not mentioned above can be clearly understood from the following description and can be more clearly understood from the embodiments set forth herein. Additionally, aspects and advantages disclosed herein can be realized via means and combinations thereof that are described in the appended claims.

In a portable air purifier according to embodiments disclosed herein, a sterilizer may be disposed on a lower side of a filter. More specifically, the sterilizer configured to irradiate light for sterilization and sterilize the filter may be disposed on or at a lower side of the filter. Additionally, the sterilizer may be disposed on an inner side of the housing, facing an inlet, and an exterior of the housing may not be scaled up despite the installation of the sterilizer, thereby making it possible to provide a compact-sized portable air purifier and sterilize the filter.

The portable air purifier according to embodiments disclosed herein may block light for sterilization aiming at the filter from being irradiated out of the housing. More specifically, a reflector may be disposed around an outer perimeter of an irradiator, and light for sterilization irradiated from the irradiator to the filter may be blocked from being irradiated out of the inlet by the reflector.

The portable air purifier according to embodiments disclosed herein may ensure an incident angle and an irradiation distance of light for sterilization aiming at the filter despite a limited size of the housing.

More specifically, the reflector disposed around the outer perimeter of the irradiator may have a funnel shape to reflect light for sterilization to the filter, and may include a reflective coating to increase reflectivity. Thus, a proper incident angle and irradiation distance of light for sterilization may be ensured.

A portable air purifier according to an embodiment may include a housing provided with an inlet forming a passage for suctioning air, a filter disposed on an upper side of the inlet and configured to purify air suctioned into the inlet and moving upward, an irradiator disposed on a lower side of the filter, installed at a height at which the irradiator overlaps the inlet and configured to irradiate light for sterilization to the filter, and a sterilizer support configured to support the irradiator, fixed to the housing, and disposed around the outer perimeter of the irradiator.

The irradiator may include a printed circuit board supported by the sterilizer support and disposed on the lower side of the filter, and a sterilizing light source disposed on the printed circuit board and configured to irradiate light for sterilization to the filter. Additionally, centers of the sterilizing light source and the filter may be aligned with each other in an upward-downward direction.

The sterilizer support may include a support body disposed around the outer perimeter of the irradiator and configured to reflect light for sterilization irradiated from the sterilizing light source to the filter. The support body may include a reflector concave toward the filter, provided with the sterilizing light source at a center thereof, and configured to reflect light irradiated from the sterilizing light source to the filter, and an inner supporter extended to a lower side of the reflector and configured to support the printed circuit board of the irradiator.

The support body may further include a heat dissipating hole including a plurality of holes on the reflector and configured to air-cool the irradiator. The heat dissipating hole may be provided with a plurality of long holes having a circular arc shape around the sterilizing light source.

The reflector may be disposed on an inner side of the housing, facing the inlet. The reflector may include a first reflecting body disposed around a perimeter of the sterilizing light source and spaced from the sterilizing light source, and a second reflecting body that extends from the first reflecting body upward at a slant.

The second reflecting body may be formed into a funnel an upper side of which is open, and may have an inner diameter that gradually increases from the first reflecting body toward the filter. The inner supporter may include an inner bracket that extends to the lower side of the reflector, and a hook bent from a lower side of the inner bracket inward to the irradiator and held at an edge of the irradiator.

The support body may further include a blocking body that extends downward from an outer edge of the reflector. The blocking body may be formed into a cylinder a lower side of which is open, and a center of the blocking body and a center of the inlet may be aligned with each other. The sterilizer support may further include a support bracket that extends to a lower side of the support body and fixed to the housing.

A portable air purifier according to another embodiment may include a first case provided therein with an accommodation space, an inlet through which air is suctioned on a lateral surface of a lower portion thereof and an outlet through which air is discharged on an upper side thereof, a second case connected to the lower portion of the first case, a filter installed inside of the first case and configured to purify air suctioned into the inlet, a fan module disposed between the filter and the outlet and configured to rotate a fan to blow air toward the outlet, an irradiator disposed on a lower side of the filter and configured to irradiate light for sterilization to the filter, and a sterilizer support configured to support the irradiator, fixed to at least one of the first case or the second case, and disposed around an outer perimeter of the irradiator. Additionally, centers of the first case, the filter, the fan module, and the irradiator may be aligned with one another in an upward-downward direction.

The sterilizer support may include a support body disposed around the outer perimeter of the irradiator and configured to reflect light for sterilization irradiated from the irradiator to the filter, and a support bracket that extends to a lower side of the support body and fixed to at least one of the first case or the second case. The support body may include a reflector concave toward the filter, provided with the irradiator at a center thereof, and configured to reflect light irradiated from the irradiator to the filter, and an inner supporter that extends to a lower side of the reflector and configured to support a printed circuit board of the irradiator.

The support body may further include a heat dissipating hole including a plurality of holes on the reflector and configured to air-cool the irradiator. Further, a reflective coating layer may be formed on a surface of the reflector.

A portable air purifier according to embodiments disclosed herein may prevent pollution of air since a filter is sterilized by light for sterilization irradiated from a sterilizer. Further, the portable air purifier according to embodiments disclosed herein may ensure space availability and have a compact size as the sterilizer is installed in a space in which an inlet is installed.

The portable air purifier according to embodiments disclosed herein may prevent light for sterilization aimed at the filter from being irradiated out of a housing such that the portable air purifier is reliably used. Also, the portable air purifier according to embodiments disclosed herein may reliably ensure an incident angle and an irradiation distance of light for sterilization even in a limited area as a result of installation of a reflector provided with a reflective coating such that the sterilizer provides improved sterilization efficiency.

The embodiments are described above with reference to a number of illustrative embodiments thereof. However, the embodiments are not intended to limit the embodiments and drawings set forth herein, and numerous other modifications and embodiments can be drawn by one skilled in the art without departing from the technical spirit. Further, the effects and predictable effects based on the configurations in the disclosure are to be included within the range of the disclosure though not explicitly described in the description of the embodiments.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present invention.

Spatially relative terms, such as "lower", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, embodiments should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A portable air purifier, comprising:
   a housing having an inlet forming a passage through which air is suctioned into the housing;
   a filter disposed at an upper side of the inlet and configured to purify air suctioned in through the inlet and flowing upward;
   an irradiator disposed at a lower side of the filter, installed at a height at which the irradiator overlaps the inlet and configured to irradiate light for sterilization onto the filter; and
   a sterilizer support configured to support the irradiator and configured to be fixed to the housing and disposed around an outer perimeter of the irradiator, wherein the irradiator comprises:
      a printed circuit board supported by the sterilizer support and disposed at the lower side of the filter; and
      a sterilizing light source disposed on the printed circuit board and configured to irradiate light for sterilization onto the filter.

2. The portable air purifier of claim 1, wherein centers of the sterilizing light source and the filter are aligned with each other along a central longitudinal axis of the portable air purifier.

3. The portable air purifier of claim 1, wherein the sterilizer support comprises:
   a support body disposed around the outer perimeter of the irradiator and configured to reflect light for sterilization irradiated from the sterilizing light source onto the filter.

4. The portable air purifier of claim 3, wherein the support body comprises:
   a reflector concave toward the filter, provided with the sterilizing light source at a center thereof, and configured to reflect the light irradiated from the sterilizing light source onto the filter; and
   an inner supporter that extends to a lower side of the reflector and configured to support the printed circuit board of the irradiator.

5. The portable air purifier of claim 4, wherein the support body further comprises:
   a plurality of heat dissipating holes formed in the reflector and configured to air-cool the irradiator.

6. The portable air purifier of claim 5, wherein the plurality of heat dissipating holes comprises a plurality of circumferentially-extending holes having a circular arc shape disposed around the sterilizing light source.

7. The portable air purifier of claim 4, wherein the reflector is disposed at an inner side of the housing, facing the inlet.

8. The portable air purifier of claim 4, wherein the reflector comprises:
   a first reflecting body provided along a perimeter of the sterilizing light source and spaced apart from the sterilizing light source; and
   a second reflecting body that extends from the first reflecting body upward at a slant.

9. The portable air purifier of claim 8, wherein the second reflecting body comprises a funnel an upper side of which is open, and having an inner diameter that gradually increases from the first reflecting body toward the filter.

10. The portable air purifier of claim 4, wherein the inner supporter comprises:
    an inner bracket that extends to the lower side of the reflector; and
    a hook bent from a lower side of the inner bracket inward toward the irradiator and configured to be held at an edge of the irradiator.

11. The portable air purifier of claim 4, wherein the support body further comprises:

a blocking body that extends downward from an outer edge of the reflector.

12. The portable air purifier of claim 11, wherein the blocking body comprises a cylinder a lower side of which is open, and wherein a center of the blocking body and a center of the inlet are aligned with each other.

13. The portable air purifier of claim 3, wherein the sterilizer support further comprises:
a support bracket that extends to a lower side of the support body and configured to be fixed to the housing.

14. A portable air purifier, comprising:
a first case including an accommodation space, an inlet through which air is suctioned into the accommodation space on a lateral surface of a lower portion thereof, and an outlet through which air is discharged on an upper side thereof;
a second case connected to the lower portion of the first case;
a filter installed inside of the first case and configured to purify air suctioned into the inlet;
a fan module disposed between the filter and the outlet and configured to rotate a fan to blow air toward the outlet;
an irradiator disposed at a lower side of the filter and configured to irradiate light for sterilization onto the filter; and
a sterilizer support configured to support the irradiator, fixed to at least one of the first case or the second case and disposed around an outer perimeter of the irradiator, wherein the irradiator comprises:
a printed circuit board supported by the sterilizer support and disposed at the lower side of the filter; and
a sterilizing light source disposed on the printed circuit board and configured to irradiate light for sterilization onto the filter.

15. The portable air purifier of claim 14, wherein centers of the first case, the filter, the fan module, and the irradiator are aligned with one another along a central longitudinal axis of the portable air purifier.

16. The portable air purifier of claim 14, wherein the sterilizer support comprises:
a support body disposed around the outer perimeter of the irradiator and configured to reflect light for sterilization irradiated from the sterilizing light source onto the filter; and
a support bracket that extends to a lower side of the support body and configured to be fixed to at least one of the first case or the second case.

17. The portable air purifier of claim 16, wherein the support body comprises:
a reflector concave toward the filter, provided with the irradiator at a center thereof, and configured to reflect the light irradiated from the sterilizing light source onto the filter; and
an inner supporter that extends to a lower side of the reflector and configured to support a printed circuit board of the irradiator.

18. The portable air purifier of claim 17, wherein the support body further comprises:
a plurality of heat dissipating holes formed in the reflector and configured to air-cool the irradiator.

19. The portable air purifier of claim 17, wherein a reflective coating layer is formed on a surface of the reflector.

20. A portable air purifier, comprising:
a housing having an inlet forming a passage through which air is suctioned into the housing;
a filter disposed at an upper side of the inlet and configured to purify air suctioned in through the inlet and flowing upward;
an irradiator disposed at a lower side of the filter, installed at a height at which the irradiator overlaps the inlet and configured to irradiate light for sterilization onto the filter, the irradiator comprising a printed circuit board supported by the sterilizer support and disposed at the lower side of the filter, and a sterilizing light source disposed on the printed circuit board and configured to irradiate light for sterilization onto the filter; and
a sterilizer support configured to support the irradiator and configured to be fixed to the housing and disposed around an outer perimeter of the irradiator, wherein the sterilizer support directs the light irradiated by the sterilizing light source onto the filter.

21. The portable air purifier of claim 20, wherein the sterilizer support comprises:
a support body disposed around the outer perimeter of the irradiator and configured to reflect the light for sterilization irradiated from the sterilizing light source onto the filter, and wherein the support body comprises:
a reflector concave toward the filter, provided with the sterilizing light source at a center thereof, and configured to reflect the light irradiated from the sterilizing light source onto the filter; and
an inner supporter that extends to a lower side of the reflector and configured to support the printed circuit board of the irradiator.

* * * * *